United States Patent
Clarke et al.

(10) Patent No.: US 8,974,809 B2
(45) Date of Patent: Mar. 10, 2015

(54) MEDICAL DEVICES HAVING A FILTER INSERT FOR CONTROLLED DIFFUSION

(75) Inventors: John Clarke, Galway (IE); Tim O'Connor, Galway (IE); Yixin Xu, Newton, MA (US); Barry J. O'Brien, Galway (IE)

(73) Assignee: Boston Scientific Scimed, Inc., Maple Grove, MN (US)

( * ) Notice: Subject to any disclaimer, the term of this patent is extended or adjusted under 35 U.S.C. 154(b) by 1173 days.

(21) Appl. No.: 11/860,188

(22) Filed: Sep. 24, 2007

(65) Prior Publication Data

US 2009/0081271 A1    Mar. 26, 2009

(51) Int. Cl.
*A61F 2/00* (2006.01)
*A61F 2/82* (2013.01)
*A61F 2/91* (2013.01)
*A61F 2/01* (2006.01)
*A61F 2/04* (2013.01)

(52) U.S. Cl.
CPC ... *A61F 2/82* (2013.01); *A61F 2/00* (2013.01); *A61F 2/91* (2013.01); *A61F 2/01* (2013.01); *A61F 2/04* (2013.01); *A61F 2250/0068* (2013.01)
USPC .......................................................... 424/423

(58) Field of Classification Search
USPC .......................................................... 424/423
See application file for complete search history.

(56) References Cited

U.S. PATENT DOCUMENTS

| | | | |
|---|---|---|---|
| 4,494,950 A * | 1/1985 | Fischell ........................... | 604/66 |
| 4,781,693 A * | 11/1988 | Martinez et al. ............... | 604/175 |
| 5,516,522 A * | 5/1996 | Peyman et al. ................ | 424/426 |
| 5,733,925 A | 3/1998 | Kunz et al. | |
| 6,517,888 B1 | 2/2003 | Weber | |
| 6,558,321 B1 * | 5/2003 | Burd et al. ..................... | 600/300 |
| 2003/0010808 A1 * | 1/2003 | Uhland et al. ................. | 228/110.1 |
| 2005/0043894 A1 * | 2/2005 | Fernandez ....................... | 702/19 |
| 2005/0119737 A1 * | 6/2005 | Bene et al. ..................... | 623/4.1 |
| 2005/0267440 A1 * | 12/2005 | Herman et al. ................ | 604/501 |
| 2006/0093646 A1 * | 5/2006 | Cima et al. ..................... | 424/425 |
| 2006/0222755 A1 | 10/2006 | Diaz et al. | |
| 2006/0293757 A1 | 12/2006 | McKay et al. | |

FOREIGN PATENT DOCUMENTS

| | | |
|---|---|---|
| DE | 10235868 A1 | 2/2004 |
| JP | 2006-055418 | 3/2006 |
| WO | 2006023286 A2 | 3/2006 |

OTHER PUBLICATIONS

L. Leoni et al. "Nanoporous Platforms for Cellular Sensing and Delivery," Sensors 2002, 2, 111-120.
T. Lippert et al., "Chemical and spectroscopic aspects of polymer ablation: Special features and novel directions," Chem. Rev., 103(2): 453-485, Feb. 2003.
J. Meijer et al., "Laser Machining by short and ultrashort pulses, state of the art and new opportunities in the age of photons," Annals of the CIRP, 51(2), 531-550, 2002.

* cited by examiner

*Primary Examiner* — Benjamin Packard
(74) *Attorney, Agent, or Firm* — Fish & Richardson P.C.

(57) ABSTRACT

An implantable or insertable medical device is provided which includes as components: (a) a substrate component comprising a depression that is at least partially filled with a therapeutic agent-containing material that comprises a first therapeutic agent, and (b) a pre-formed filter insert disposed in the depression such that it regulates transport of chemical species between the depression and the exterior of the device upon implantation or insertion of the device in vivo.

23 Claims, 10 Drawing Sheets

MEDICAL DEVICES HAVING A FILTER INSERT FOR CONTROLLED DIFFUSION

TECHNICAL FIELD

This invention relates to medical devices, and more particularly, to medical devices that utilize filter inserts to control the release of one or more therapeutic agents.

BACKGROUND OF THE INVENTION

The in-situ delivery of therapeutic agents within the body of a patient is common in the practice of modern medicine. In-situ delivery of therapeutic agents is often implemented using medical devices that may be temporarily or permanently placed at a target site within the body. These medical devices can be maintained, as required, at their target sites for short or prolonged periods of time in order to deliver therapeutic agents to the target site.

In some cases however, delivery of the biologically active material to the body tissue immediately after insertion or implantation of the medical device may not be needed or desired. For instance, if a stent is used to prevent the occurrence of restenosis after balloon angioplasty, it may be desirable to ensure that the drug continues to be released when restenosis occurs or begins to occur in a body lumen that has been stented with a drug-coated stent. Therefore, there is a need for insertable or implantable medical devices that can provide delayed and/or controlled, continuous delivery of biologically active materials when such materials are required by the patient after implantation of the medical device.

Current techniques for the in-situ delivery of therapeutic agents in a controlled manner often involve the use of a polymer coating on the insertable or implanatable medical device to contain the agents and control its release rate. The polymer coating, however, may sometimes be a contributing factor in causing an inflammatory response in the tissue with which it comes in contact. For instance, when a Drug Eluting Stent (DES) is implanted in a vessel, the inflammatory response which sometimes arises can cause a reduction in the diameter of the vessel lumen within the stent. The inflammatory response can lead to late in stent thrombosis.

SUMMARY OF THE INVENTION

In accordance with the present invention, an implantable or insertable medical device is provided which includes as components: (a) a substrate component comprising a depression that is at least partially filled with a therapeutic agent-containing material that comprises a first therapeutic agent, and (b) a pre-formed filter insert disposed in the depression such that it regulates transport of chemical species between the depression and the exterior of the device upon implantation or insertion of the device in vivo.

In accordance with one aspect of the invention, the pre-formed filter insert may be disposed in the depression over the therapeutic agent-containing material.

In accordance with another aspect of the invention, the pre-formed filter insert may be impregnated with the therapeutic agent-containing material.

In accordance with another aspect of the invention, a welded braze may secure the filter insert in the depression.

In accordance with another aspect of the invention, the pre-formed filter insert may be configured so that it is secured in the depression by an interference fit.

In accordance with another aspect of the invention, an opening into the depression may have a peripheral lip that engages with the filter insert to secure the filter insert within the depression.

In accordance with another aspect of the invention, the filter insert may include an assembly having a porous base and at least one channel extending through the assembly to the porous base through which the porous base is loaded with the therapeutic agent-containing material.

In accordance with another aspect of the invention, the substrate component may comprise a plurality of depressions.

In accordance with another aspect of the invention, the depression may be a blind hole or a trench.

In accordance with another aspect of the invention, the medical device may be adapted for implantation or insertion into the coronary vasculature, peripheral vascular system, esophagus, trachea, colon, biliary tract, urogenital system, or brain.

In accordance with another aspect of the invention, the medical device may be selected from a drug delivery device, an implant, a stent, a graft, a filter, a catheter, a defibrillator, a chronic rhythm management lead and a neuromodulation device.

In accordance with another aspect of the invention, the therapeutic-agent-containing material may further comprise a material in addition to said first therapeutic agent.

In accordance with another aspect of the invention, the therapeutic-agent-containing material may further comprise a second therapeutic agent.

In accordance with another aspect of the invention, the pre-formed filter insert may includes a nanoporous region.

In accordance with another aspect of the invention, the smallest lateral dimension of the depression may be less than 10,000 microns.

These and other embodiments and advantages of the present invention will become readily apparent to those of ordinary skill in the art upon review of the Detailed Description and Claims to follow.

DETAILED DESCRIPTION

According to an aspect of the present invention, implantable or insertable medical devices are provided which contain the following: (a) a substrate having one or more depressions that contain at least one therapeutic agent and (b) one or more pre-formed filter inserts located in the depression to regulate transport of chemical species (e.g., in many embodiments, the therapeutic agent, among others) between the therapeutic-agent-containing depressions and the exterior of the device. The pre-formed filter inserts serve as a membrane through which the chemical species diffuses. In some embodiments of the invention the filter insert may also serve as a reservoir in which the therapeutic agent is impregnated. The use of a pre-formed filter insert can advantageously avoid the use of a polymer coating to control the release of the chemical species.

Implantable or insertable medical devices which can be constructed in accordance with the invention vary widely and include, for example, stents (including coronary vascular stents, peripheral vascular stents, cerebral, urethral, ureteral, biliary, tracheal, gastrointestinal and esophageal stents), stent coverings, stent grafts, vascular grafts, abdominal aortic aneurysm (AAA) devices (e.g., AAA stents, AAA grafts), vascular access ports, dialysis ports, catheters (e.g., urological catheters or vascular catheters such as balloon catheters and various central venous catheters), guide wires, filters (e.g., vena cava filters and mesh filters for distil protection devices), embolization devices including cerebral aneurysm filler coils (including Guglilmi detachable coils and metal coils), septal defect closure devices, drug depots that are adapted for placement in an artery for treatment of the portion of the artery distal to the device, myocardial plugs, pacemakers, leads including pacemaker leads, defibrillation leads, and coils, ventricular assist devices including left ventricular assist hearts and pumps, total artificial hearts, shunts, valves including heart valves and vascular valves, anastomosis clips and rings, cochlear implants, tissue bulking devices, and tissue engineering scaffolds for cartilage, bone, skin and other in vivo tissue regeneration, sutures, suture anchors, tissue staples and ligating clips at surgical sites, cannulae, metal wire ligatures, urethral slings, hernia "meshes", artificial ligaments, orthopedic prosthesis such as bone grafts, bone plates, fins and fusion devices, joint prostheses, orthopedic fixation devices such as interference screws in the ankle, knee, and hand areas, tacks for ligament attachment and meniscal repair, rods and pins for fracture fixation, screws and plates for craniomaxillofacial repair, dental implants, or other devices that are implanted or inserted into the body.

The medical devices of the present invention include, for example, implantable and insertable medical devices that are used for systemic diagnosis or treatment, as well as those that are used for the localized diagnosis or treatment of any mammalian tissue or organ. Non-limiting examples are tumors; organs including the heart, coronary and peripheral vascular system (referred to overall as "the vasculature"), the urogenital system, including kidneys, bladder, urethra, ureters, prostate, vagina, uterus and ovaries, eyes, ears, spine, nervous system, lungs, trachea, esophagus, intestines, stomach, brain, liver and pancreas, skeletal muscle, smooth muscle, breast, dermal tissue, cartilage, tooth and bone.

Medical devices benefiting from the present invention thus include a variety of implantable and insertable medical devices including devices for insertion into and/or through a wide range of body lumens, for purposes of diagnosis or treatment, several of which are recited above, including lumens of the cardiovascular system such as the heart, arteries (e.g., coronary, femoral, aorta, iliac, carotid and vertebrobasilar arteries) and veins, lumens of the genitourinary system such as the urethra (including prostatic urethra), bladder, ureters, vagina, uterus, spermatic and fallopian tubes, the nasolacrimal duct, the eustachian tube, lumens of the respiratory tract such as the trachea, bronchi, nasal passages and sinuses, lumens of the gastrointestinal tract such as the esophagus, gut, duodenum, small intestine, large intestine, rectum, biliary and pancreatic duct systems, lumens of the lymphatic system, the major body cavities (peritoneal, pleural, pericardial) and so forth.

As used herein, terms such as "treatment" and "therapy" refers to the prevention of a disease or condition, the reduction or elimination of symptoms associated with a disease or condition, or the substantial or complete elimination of a disease or condition.

Preferred subjects for treatment or diagnosis are vertebrate subjects, for example, humans, livestock and pets.

In some embodiments, the substrate from which the medical device is formed has a tubular configuration (e.g., stents, tubing, etc.). In such embodiments, the one or more depressions may be provided within the abluminal surface of the tubular substrate. Alternatively, the one or more depressions may be provided within the luminal surface of the tubular substrate. As another alternative, among others, the one or more depressions may be provided within each of the luminal and abluminal surfaces of the tubular substrate.

Figure 1A:
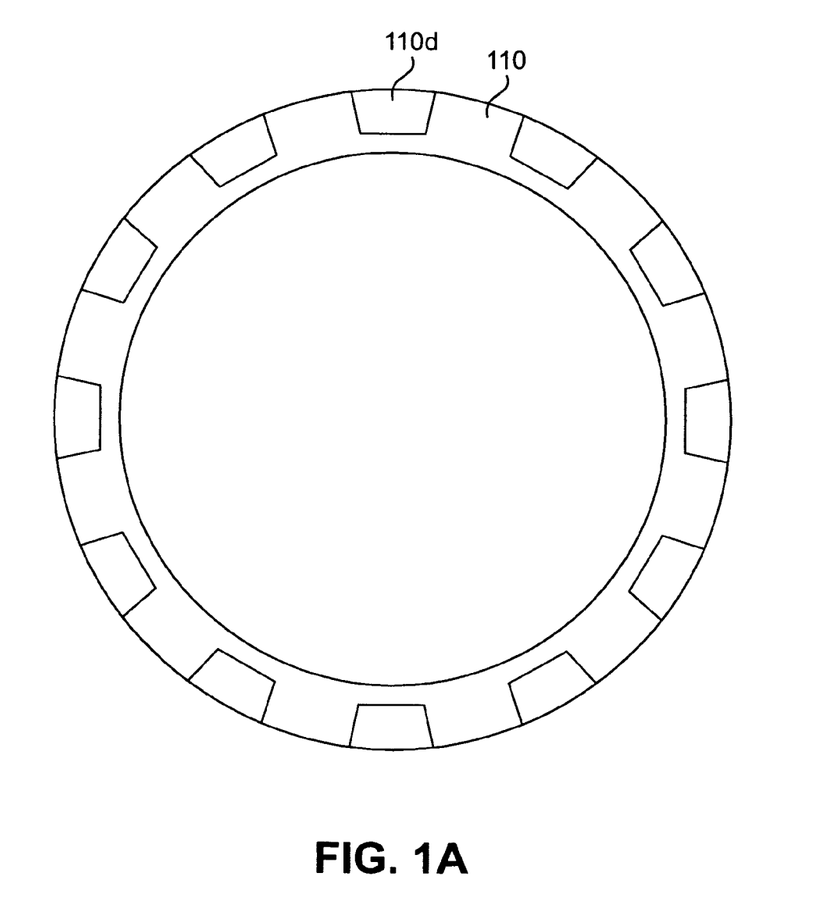
FIG. 1A is a schematic cross-sectional view illustrating a substrate from which a tubular medical device may be formed in accordance with an embodiment of the invention.
Figure 1B:
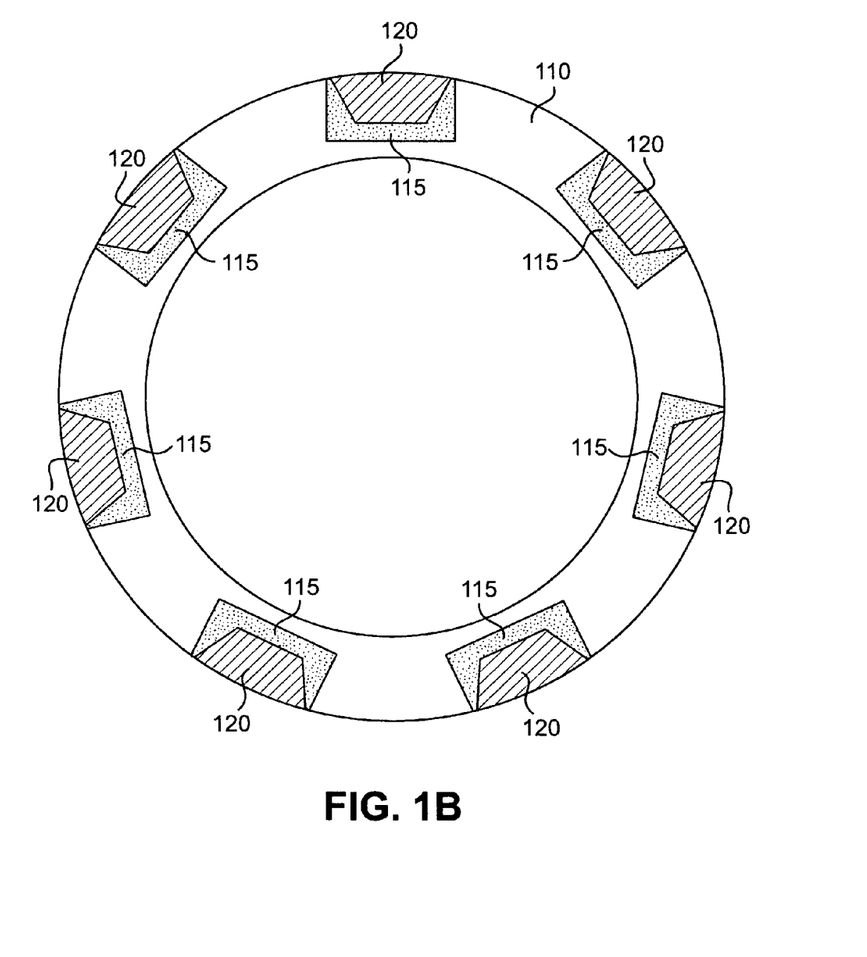
FIG. 1B is a schematic cross-sectional view illustrating one example of a filter insert that may be fitted into the depressions of the substrate shown in FIG. 1A.

By way of example, FIG. 1A is a schematic cross-section illustrating a tubular medical device substrate 110, which contains depressions 110d on its outer (abluminal) surface, which can be filled with a therapeutic-agent-containing composition 115 as shown in FIG. 1B. The depressions can be loaded with the composition 115 using, for instance, solvent carriers and evaporation techniques. Alternatively, the composition 115 can be loaded as crystalline or amorphous powder. The therapeutic-agent-containing composition 115 may consist essentially of one or more therapeutic agents, or it may contain further optional agents such as polymer matrix materials, diluents, excipients or fillers. Moreover, all of the depressions 110d may be filled with the same therapeutic-agent-containing composition 115, or some depressions may be filled with a first therapeutic-agent-containing composition while other depressions may be filled with a different therapeutic-agent-containing composition, among other possibilities. A pre-formed filter insert 120 is located in each of the depressions 110d over the therapeutic-agent-containing composition 115.

The pre-formed filter inserts 120 may be secured in the depressions 110d by any of a variety of different means. For example, in FIG. 3A the filter insert 120 is held in place by a welded braze 122 that is formed by welding a non-polymeric biocompatible material using, for example, a pulsed laser welding technique. The welded braze 122 will hold the filter in place and prevent the therapeutic-agent-containing composition 115 from escaping past the sides of the filter insert

Figure 3A:
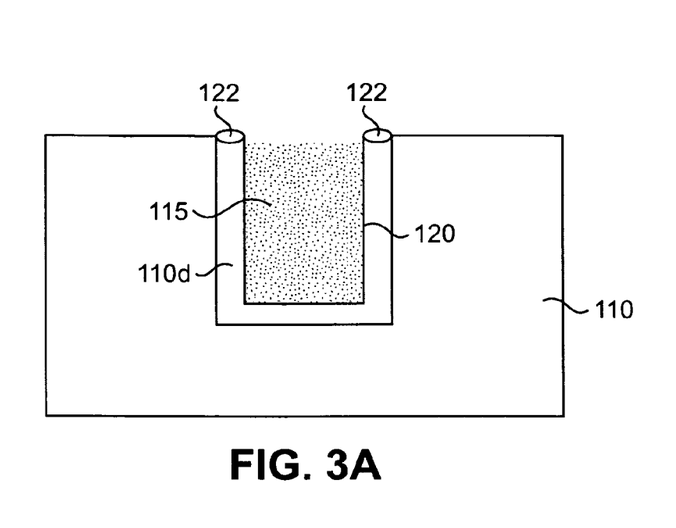
FIG. 3A is a schematic cross-sectional view taken along line b-b of FIG. 2A showing one embodiment of the filter insert that is welded to the substrate.

120. In this way the therapeutic-agent-containing composition 115 can only escape from the depressions 110d through the filter inserts 120.

Figure 1C:
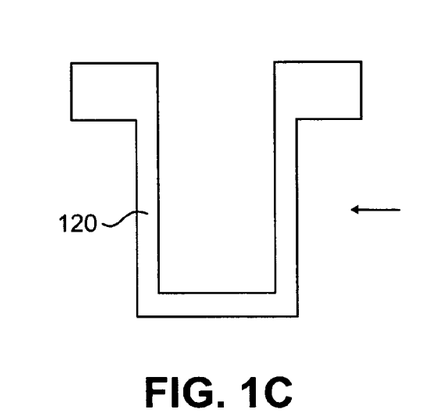
FIGS. 1C-1E are schematic cross-section views illustrating various embodiments of the filter insert that may be employed in the present invention.
Figure 1D:
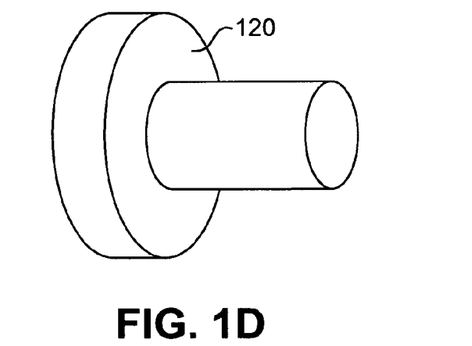

Another arrangement for securing the filter inserts 120 in the depressions 110d is shown in FIG. 1B. In this example the filter inserts 120 are tapered to provide an interference fit in the depressions 110d. Instead of a taper, an interference fit may be achieved by using filter inserts 120 with other configurations, examples of which are shown in FIGS. 1C and 1D.

Figure 1E:
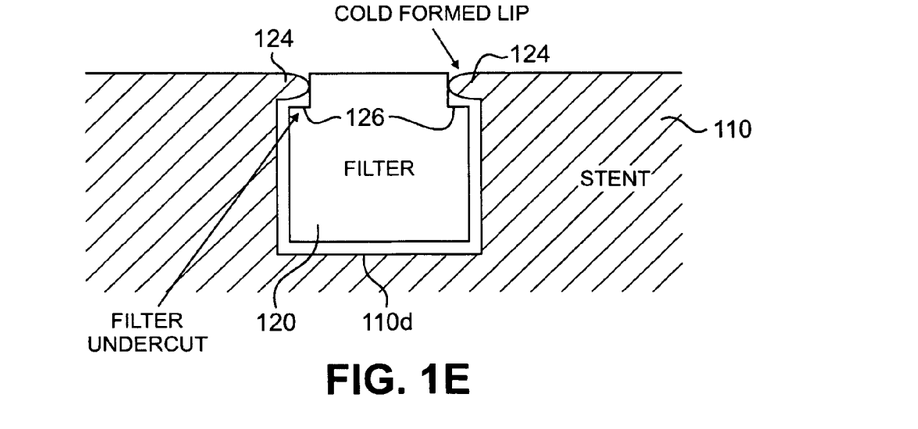

FIG. 1E shows another arrangement for securing the filter inserts 120 in the depressions 110d. FIG. 1E shows only a single depression 110d in a segment of the substrate 110. In this example a lip or burr 124 is provided on the outer surface of the substrate 110 along the periphery of the depressions 110d. The filter insert 120 is provided with an undercut 126 that engages with the lip or burr 124. The filter insert 120 is then inserted into the depression 110d and the stent material and the lip or burr 120 is peened over the filter undercut 126. The lip or burr 124 can be formed, for example, in a cold forming process using a micro-press tool that is made from a material that is significantly harder than the material from which the substrate 110 is formed.

Figure 8:
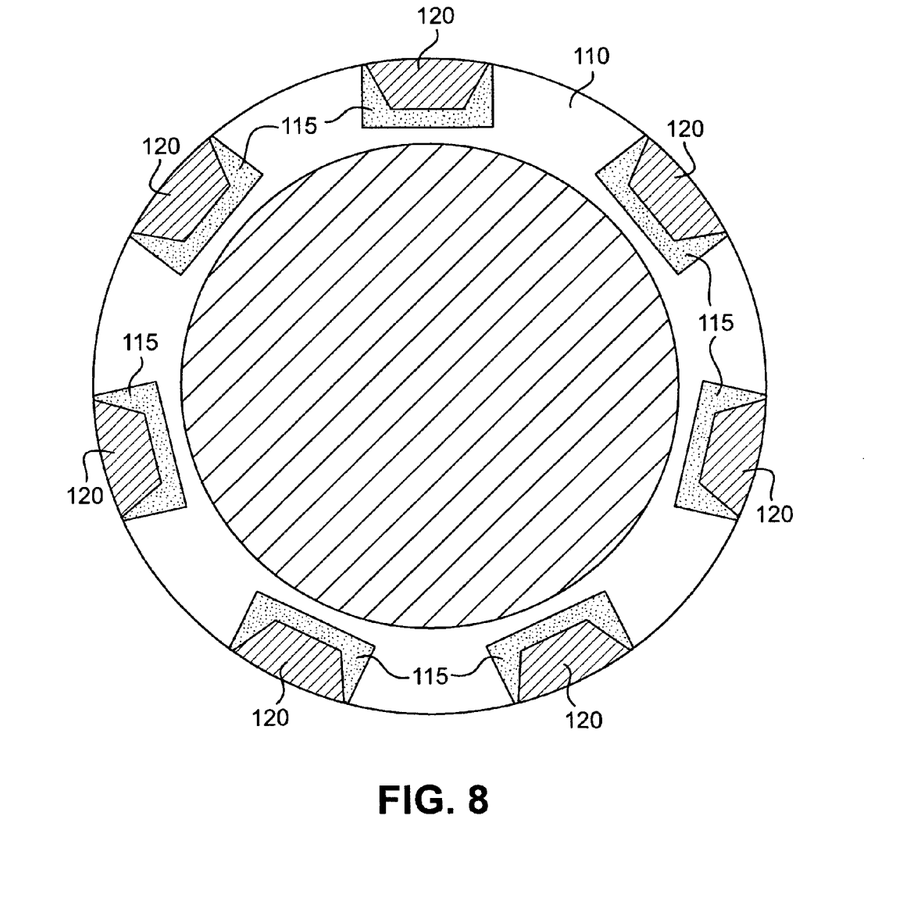

A schematic cross-sectional illustration of another substrate that may be employed is shown in FIG. 8. This substrate is similar to that of FIGS. 1A-1E, except that the substrate 110 is of circular (solid) cross-section rather than annular (hollow) cross-section. Examples of medical devices that can be formed from this type of substrate include, for example, embolic spheres, embolic rods, and orthopedic implants, among many others.

Figure 2A:
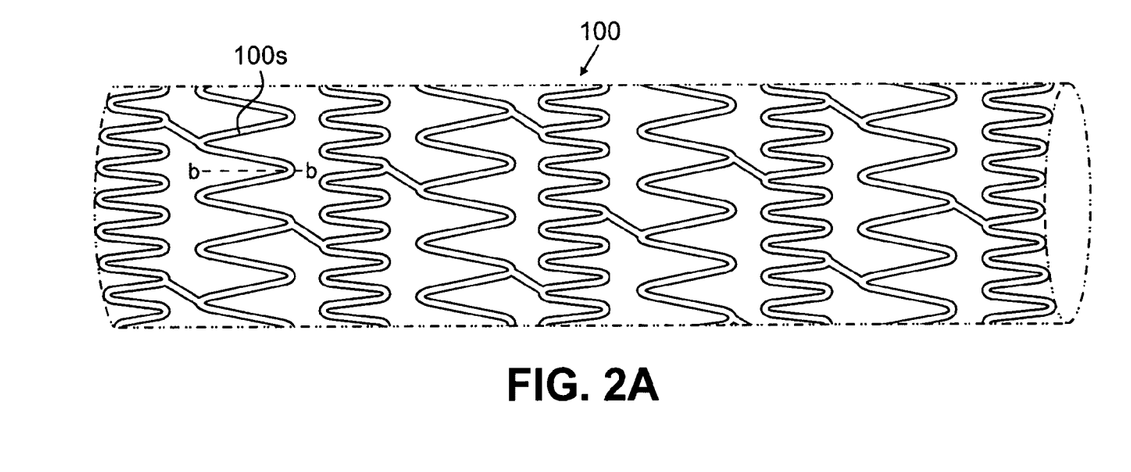
FIG. 2A is a schematic perspective view of a stent in accordance with an embodiment of the invention.
Figure 2B:
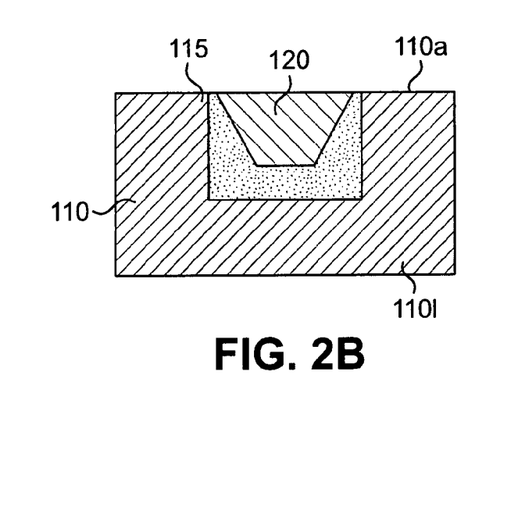
FIG. 2B is a schematic cross-sectional view taken along line b-b of FIG. 2A.
Figure 2C:
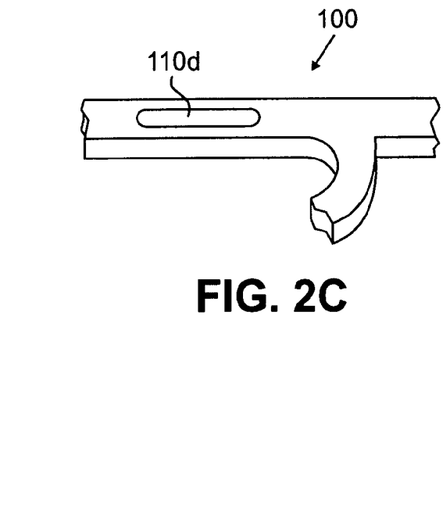
FIG. 2C is a schematic perspective view of a portion of the stent of FIG. 2A.

One example of medical device that may be formed from the tubular substrate shown in FIGS. 1A-1E is a stent. FIG. 2A shows a schematic perspective view of an illustrative stent 100 which contains a number of interconnected struts 100s. FIG. 2B is a cross-section taken along line b-b of strut 100s of stent 100 of FIG. 2A, which has an abluminal surface 100a and a luminal surface 100l. The following are shown in FIG. 2B: a strut substrate 110, a depression 110d, which is filled with a therapeutic-agent-containing composition 115, and a pre-formed filter insert 120 that is disposed in the depression 110d over the therapeutic-agent-containing composition 115. FIG. 2C is a perspective view of a portion of the stent 100 in FIG. 2A (designated by reference letter c) to shown the shape of the depression in the substrate 110.

In the embodiments of the invention described above the pre-formed filter insert 120 largely serves as a membrane to control the diffusion rate of the therapeutic-agent-containing composition 115 out of the depression 110d. In other embodiments of the invention, however, the pre-formed filter insert 120 may also serve as a reservoir in which the therapeutic-agent-containing composition 115 can be located. For instance, turning to FIG. 3A, which is a cross-section taken along line b-b of strut 100s of stent 100, the therapeutic-agent-containing composition 115 is loaded in the filter insert 120 so that the filter insert 120 acts as a reservoir for the composition 115. When the filter insert 120 serves as both a membrane and a reservoir, its configuration and the manner in which it is secured in the depression 110d may be similar to any of those described above when the filter insert 120 serves largely as a membrane. Of course, the filter insert 120 must have a sufficient thickness and porosity to retain an adequate amount of the therapeutic-agent-containing composition 115.

One advantage that arises from the use of a pre-formed filter insert 120 that acts as both a membrane and a reservoir is that the filter insert 120 can be pre-loaded with the therapeutic-agent-containing composition 115 before the filter insert 120 is installed in the depression 110d. Pre-loading the therapeutic-agent-containing composition 115 in the filter insert 120 allows for better control when impregnating the filter insert 120 with the therapeutic-agent-containing composition 115 using, for example, a syringe.

Figure 3B:
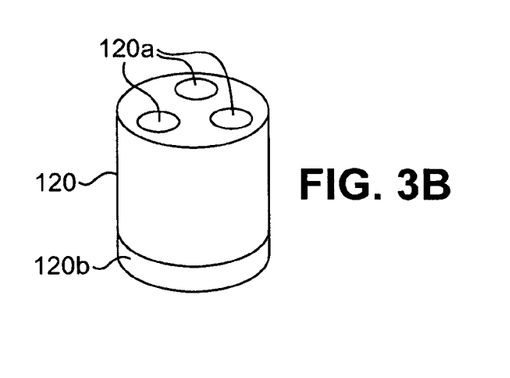
FIG. 3B is a schematic perspective view of another embodiment of the filter insert.
Figure 3C:
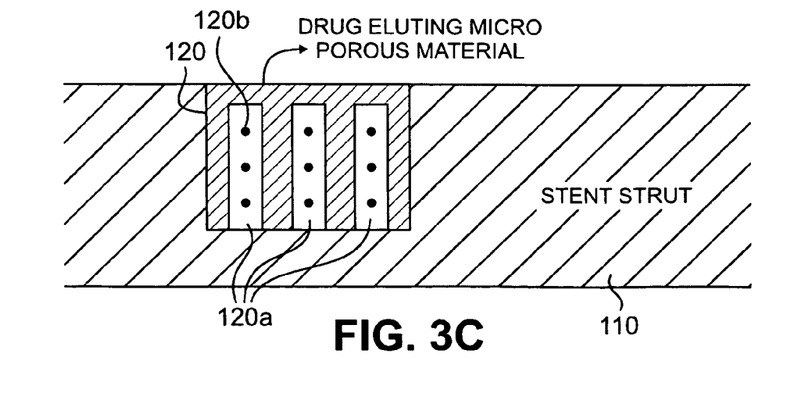
FIG. 3C is a schematic cross-section view of the filter insert depicted in FIG. 3B after it has been inserted into a depression of a substrate.

One particular example of a filter insert 120 that acts as both a membrane and a reservoir is shown in perspective in FIG. 3B. In this example the filter insert 120 includes one or more channels 120a that extend to a porous base 120b. The porous base 120b of the filter insert 120 may be impregnated with the therapeutic-agent-containing composition 115 by applying the composition 115 through the channels from the top of the filter insert 120. Once the therapeutic-agent-containing composition 115 is loaded, the filter insert 120 is inverted and inserted into the depression 110d of the substrate 110. FIG. 3C shows the filter insert 120 once it has been inserted into the depression 110d. In this way the therapeutic-agent-containing composition 115 can be released from the filter insert 120 to the exterior of the substrate 110 in a controlled manner.

Figure 3D:
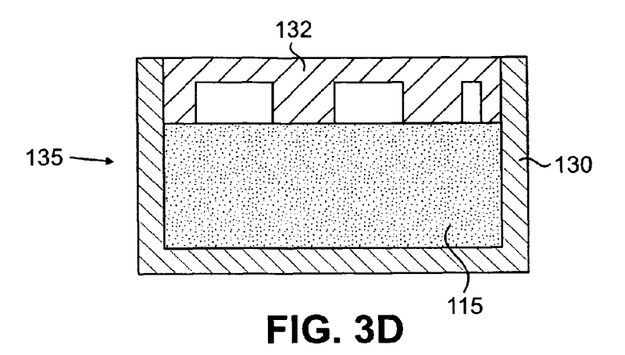
FIG. 3D is a schematic cross-sectional view of yet another embodiment of the filter insert.

FIG. 3D shows another example of a filter insert that can be pre-loaded with the therapeutic-agent-containing composition 115 and thus serves as both a membrane and a reservoir. As shown in cross-section, the filter insert is formed from an assembly 135 that includes a reservoir 130 that holds the therapeutic-agent-containing composition 115. The reservoir 130 is geometrically sized to fit within the depressions 110d and may be formed from a variety of materials such as stainless steel, for example. For instance, if the depressions 110d have a cylindrical configuration, then the reservoir 130 may have a cylindrical configuration as well. After the therapeutic-agent-containing composition 115 is loaded into the reservoir 130, a suitable filter material 132 that functions as a plug can be inserted into the top opening of the reservoir to complete the assembly 135. Finally, the assembly 135 is inserted into the depression. The assembly 135 may be form fitted or welded to the depression to secure it within the depression. Alternatively, the assembly 35 may be secured within the depression by any suitable means.

In the medical devices of the present invention, transport of species into the therapeutic-agent-containing depressions, from these depressions, or both, is regulated by the porous regions in the filter insert. The pores of these transport-controlling regions are generally substantially smaller than the smallest lateral dimensions (e.g., smaller than the width of a hole or trench, etc.) of the therapeutic-agent-containing depressions over which they are positioned. The pores of the release-controlling regions may be parallel to one another, they may be interconnected or both. They may be regular (e.g., cylindrical, etc.) or irregular in geometry.

The filter inserts are not limited to any particular material and can be selected from a range of materials, including ceramics, metals, polymers, as well as a variety of other suitable organic and inorganic materials. Because the filter inserts are pre-formed before they are inserted into the substrate, they can be formed using a wider variety of materials and techniques than could be employed if a filter were to be fabricated directly in or over the depressions in the substrate. In some cases commercially available filter inserts may be adapted for use in the present invention. For example, ceramic filter inserts are available from Tami Industries, which are typically used for purification purposes, but which can be adapted for use in the present invention if supplied with sufficiently small geometries so that they fit within the depressions.

In some embodiments of the invention the porous regions of the filter inserts may contain nanopores. A "nanopore" is a void having at least one dimension (e.g., pore width) that does not exceed about 100 nm in length. Typically nanopores have at least two orthogonal (i.e., perpendicular) dimensions that do not exceed 100 nm and a third orthogonal dimension, which can be greater than 100 nm. Nanoporous regions may further comprise pores that are not nanopores.

Figure 7:
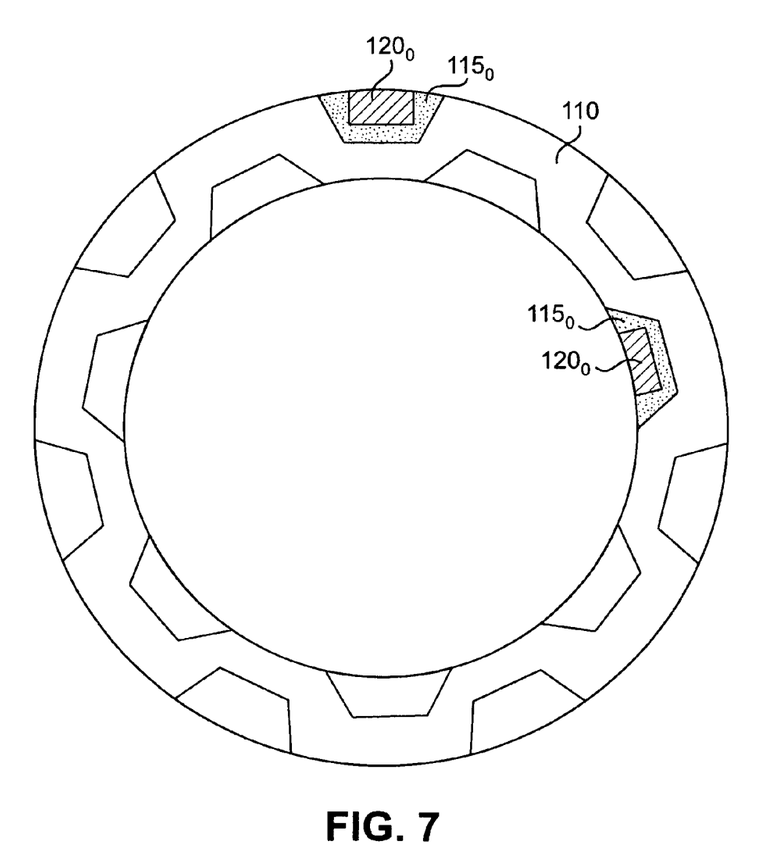
FIGS. 7-8 are various alternative embodiments of a tubular medical device that may be formed in accordance with the invention.

As indicated above, it is possible to provide different therapeutic agents at different locations on the substrate. In an embodiment like that of FIG. 7, for example, it is possible to provide one or more first depressions that are filled with a first therapeutic agent 115i (e.g., an anti-inflammatory agent, an endothelialization promoter or an antithrombotic agent) at the inner, luminal surface of the substrate 110, and one or more second depressions filled with a second therapeutic agent 115o that differs from the first therapeutic agent (e.g., an anti-restenotic agent) at the outer, abluminal surface of the substrate 110.

The substrate 110 may have single or multiple (e.g., 1 to 2 to 5 to 10 to 25 to 50 to 100 or more) therapeutic-agent-containing depressions. Therapeutic-agent-containing depression(s) may be provided over the entire device or only over one or more distinct portions of the device. For example, as seen from the above, for tubular devices such as stents, therapeutic-agent-filled depression(s) with associated filter inserts may be provided on the luminal device surfaces, on the abluminal device surfaces, on the side surface, or a combination of two or more of the luminal, abluminal and side surfaces.

Figure 4A:
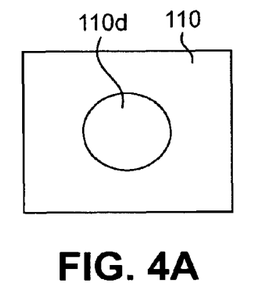
FIGS. 4A-4G and 5A-5E are schematic top views illustrating various depression configurations and arrays of the same, which may be employed in various embodiments of the invention.
Figure 4B:
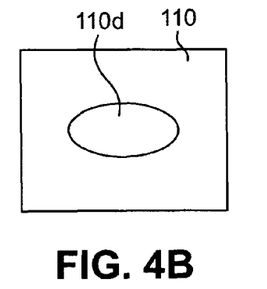
Figure 4C:
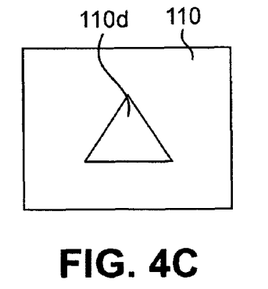
Figure 4D:
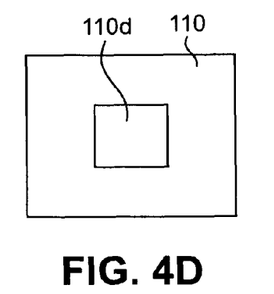
Figure 4E:
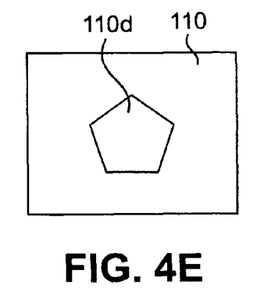
Figure 4F:
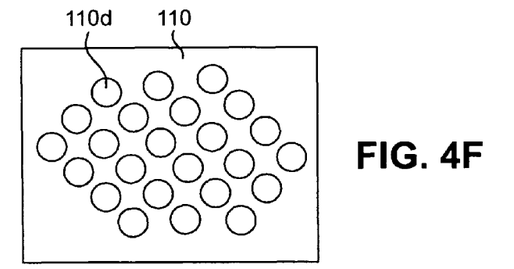
Figure 4G:
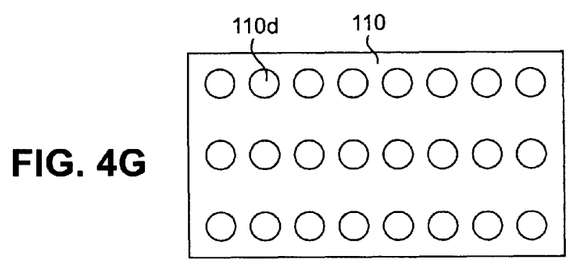
Figure 5A:
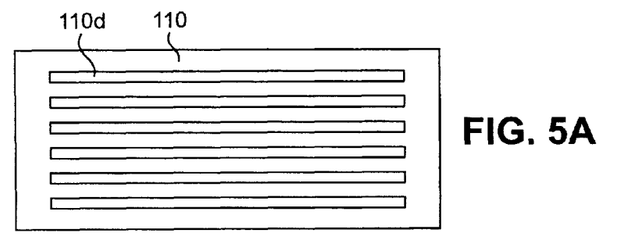
Figure 5B:
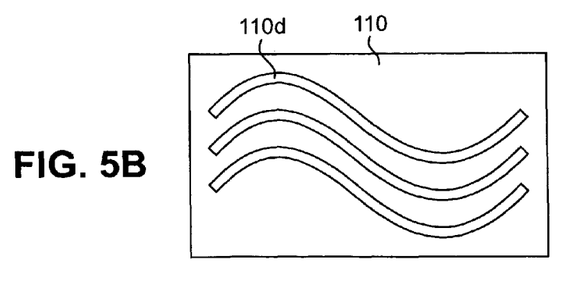
Figure 5C:
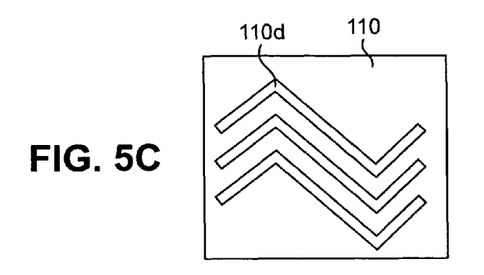
Figure 5D:
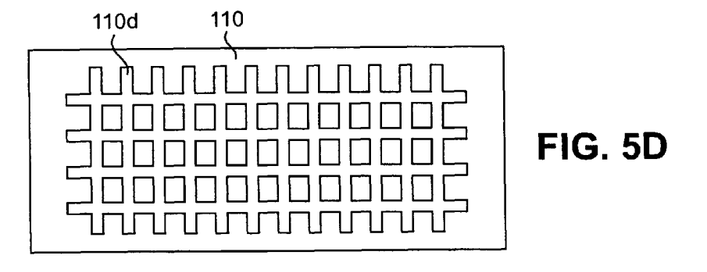
Figure 5E:
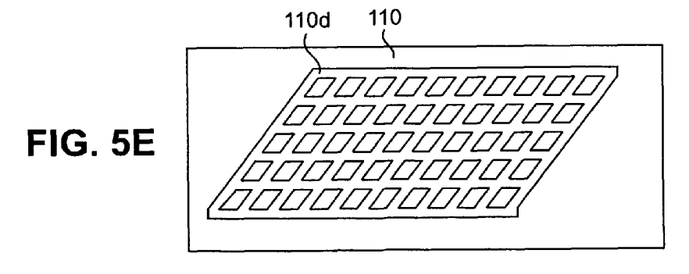

The depressions 110d which contain the therapeutic agents may come in various shapes and sizes. Examples include depressions whose lateral dimensions are circular (see, e.g., the top view of the circular hole of FIG. 4A, in which the depressed area 110d within the medical device substrate 110 is designated with a darker shade of grey), oval (see FIG. 4B), polygonal, for instance triangular (see FIG. 4C), quadrilateral (see FIG. 4D), penta-lateral (see FIG. 4E), as well as depressions of various other regular and irregular shapes and sizes. Multiple depressions 110d can be provided in a near infinite variety of arrays. See, e.g., the depressions 110d shown in FIGS. 4F and 4G. Further examples of depressions 110d include trenches, such as simple linear trenches (see FIG. 5A), wavy trenches (see FIG. 5B), trenches formed from linear segments whose direction undergoes an angular change (see FIG. 5C), trench networks intersecting at right angles (see FIG. 5D), as well as other angles (see FIG. 5E), as well as other regular and irregular trench configurations.

The therapeutic agent-containing depressions can be of any size that provides the features of the invention. Commonly, the medical devices of the invention contain therapeutic agent-containing depressions whose smallest lateral dimension (e.g., the diameter for a cylindrical depression, the width for an elongated depression such a trench, etc.) is less than 10 mm (10000 μm), for example, ranging from 10,000 μm to 5000 μm to 2500 μm to 1000 μm to 500 μm to 250 μm to 100 μm to 50 μm to 10 μm to 5 μm to 2.5 μm to 1 μm or less.

Figure 6A:
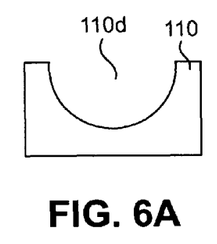
FIGS. 6A-6E are schematic cross-sectional views illustrating various depression configurations, which may be employed in various embodiments of the invention.
Figure 6B:
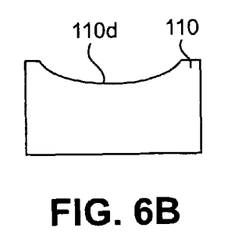
Figure 6C:
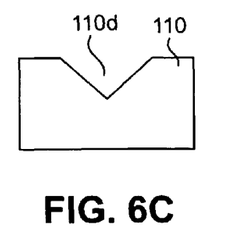
Figure 6D:
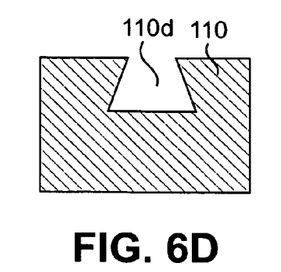
Figure 6E:
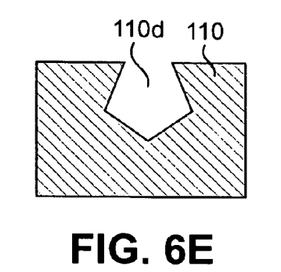

As indicated above, the depressions 110d may be in the form of blind holes, through-holes, trenches, etc. Such depressions 110d may have a variety of cross-sections, such as semicircular cross-sections (see, e.g., FIG. 6A), semi-oval cross-sections (see, e.g., FIG. 6B), polygonal cross-sections, including triangular (see, e.g., FIG. 6C), quadrilateral (see, e.g., FIG. 6D) and penta-lateral (see, e.g., FIG. 6E) cross-sections, as well as other regular and irregular cross-sections. In certain embodiments, the depressions are high aspect ratio depressions, meaning that the depth of the depression is greater than the width of the depression, for example, ranging from 1.5 to 2 to 2.5 to 5 to 10 to 25 or more times the width.

In certain other embodiments, the depressions are low aspect ratio depressions, meaning that the depth of the depression is less than the width of the depression, for example, ranging from 0.75 to 0.5 to 0.4 to 0.2 to 0.1 to 0.04 or less times the width.

Examples of techniques for forming depressions in substrates (e.g., holes, trenches, etc.), include molding techniques, direct removal techniques, and mask-based removal techniques. In molding techniques, a mold may be provided with various protrusions, which after casting the substrate of interest, create depressions in the substrate. Various direct and mask-based removal techniques are discussed below.

As previously indicated, in the present invention, the depressions further contain (i.e., they are at least partially filled with) one or more therapeutic agents that may be used singly or in combination. The therapeutic agents may be present in pure form or admixed with another material, for example, a diluent, filler, excipient, matrix material, etc. Materials for these purposes may be selected, for example, from suitable members of the polymers listed below, among many other possible materials (e.g., small molecule chemical species). Where therapeutic agents are used in combination, one therapeutic agent may provide a matrix for another therapeutic agent.

By varying the size (i.e., volume) and number of the depressions, as well as the concentration of the therapeutic agents within the depressions, a range of therapeutic agent loading levels can be achieved. The amount of loading may be determined by those of ordinary skill in the art and may ultimately depend, for example, upon the disease or condition being treated, the age, sex and health of the subject, the nature (e.g., potency) of the therapeutic agent, or other factors.

The substrate material in which the depressions are formed may vary widely in composition and is not limited to any particular material. For example, the substrate material can be selected from a range of biostable materials and biodisintegrable materials, including (a) organic materials (i.e., materials containing organic species, typically 50 wt % or more, for example, from 50 wt % to 75 wt % to 90 wt % to 95 wt % to 97.5 wt % to 99 wt % or more) such as polymeric materials and biologics, (b) inorganic materials (i.e., materials containing inorganic species, typically 50 wt % or more, for example, from 50 wt % to 75 wt % to 90 wt % to 95 wt % to 97.5 wt % to 99 wt % or more), such as metallic materials (i.e., materials containing metals, typically 50 wt % or more, for example, from 50 wt % to 75 wt % to 90 wt % to 95 wt % to 97.5 wt % to 99 wt % or more) and non-metallic inorganic materials (i.e., materials containing non-metallic inorganic materials, typically 50 wt % or more, for example, from 50 wt % to 75 wt % to 90 wt % to 95 wt % to 97.5 wt % to 99 wt % or more) (e.g., carbon, semiconductors, glasses and ceramics, which may contain various metal- and non-metal-oxides, various metal- and non-metal-nitrides, various metal- and non-metal-carbides, various metal- and non-metal-borides, various metal- and non-metal-phosphates, and various metal- and non-metal-sulfides, among others), and (c) hybrid materials (e.g., hybrid organic-inorganic materials, for instance, polymer/metallic inorganic and polymer/non-metallic inorganic hybrids).

Specific examples of non-metallic inorganic materials may be selected, for example, from materials containing one or more of the following: metal oxides, including aluminum oxides and transition metal oxides (e.g., oxides of titanium, zirconium, hafnium, tantalum, molybdenum, tungsten, rhenium, iron, niobium, and iridium); silicon; silicon-based ceramics, such as those containing silicon nitrides, silicon carbides and silicon oxides (sometimes referred to as glass ceramics); calcium phosphate ceramics (e.g., hydroxyapatite); carbon; and carbon-based, ceramic-like materials such as carbon nitrides.

Specific examples of metallic inorganic materials may be selected, for example, from metals (e.g., metals such as gold, niobium, platinum, palladium, iridium, osmium, rhodium, titanium, tantalum, tungsten, ruthenium, iron, zinc and magnesium), metal alloys comprising iron and chromium (e.g., stainless steels, including platinum-enriched radiopaque stainless steel), alloys comprising nickel and titanium (e.g., Nitinol), alloys comprising cobalt and chromium, including alloys that comprise cobalt, chromium and iron (e.g., elgiloy alloys), alloys comprising nickel, cobalt and chromium (e.g., MP 35N), alloys comprising cobalt, chromium, tungsten and nickel (e.g., L605), alloys comprising nickel and chromium (e.g., inconel alloys), and biodegradable alloys of magnesium, zinc and/or iron.

As previously noted, in some embodiments of the invention, the therapeutic-agent releasing medical device is preferably polymer-free. However, in other embodiments the substrate from which medical device is fabricated may be formed from polymers (biostable or biodegradable) as well as other high molecular weight organic materials, and may be selected, for example, from suitable materials containing one or more of the following: polycarboxylic acid polymers and copolymers including polyacrylic acids; acetal polymers and copolymers; acrylate and methacrylate polymers and copolymers (e.g., n-butyl methacrylate); cellulosic polymers and copolymers, including cellulose acetates, cellulose nitrates, cellulose propionates, cellulose acetate butyrates, cellophanes, rayons, rayon triacetates, and cellulose ethers such as carboxymethyl celluloses and hydroxyalkyl celluloses; polyoxymethylene polymers and copolymers; polyimide polymers and copolymers such as polyether block imides, polyamidimides, polyesterimides, and polyetherimides; polysulfone polymers and copolymers including polyarylsulfones and polyethersulfones; polyamide polymers and copolymers including nylon 6,6, nylon 12, polyether-block co-polyamide polymers (e.g., Pebax® resins), polycaprolactams and polyacrylamides; resins including alkyd resins, phenolic resins, urea resins, melamine resins, epoxy resins, allyl resins and epoxide resins; polycarbonates; polyacrylonitriles; polyvinylpyrrolidones (cross-linked and otherwise); polymers and copolymers of vinyl monomers including polyvinyl alcohols, polyvinyl halides such as polyvinyl chlorides, ethylene-vinylacetate copolymers (EVA), polyvinylidene chlorides, polyvinyl ethers such as polyvinyl methyl ethers, vinyl aromatic polymers and copolymers such as polystyrenes, styrene-maleic anhydride copolymers, vinyl aromatic-hydrocarbon copolymers including styrene-butadiene copolymers, styrene-ethylene-butylene copolymers (e.g., a polystyrene-polyethylene/butylene-polystyrene (SEBS) copolymer, available as Kraton® G series polymers), styrene-isoprene copolymers (e.g., polystyrene-polyisoprene-polystyrene), acrylonitrile-styrene copolymers, acrylonitrile-butadiene-styrene copolymers, styrene-butadiene copolymers and styrene-isobutylene copolymers (e.g., polyisobutylene-polystyrene block copolymers such as SIBS), polyvinyl ketones, polyvinylcarbazoles, and polyvinyl esters such as polyvinyl acetates; polybenzimidazoles; ionomers; polyalkyl oxide polymers and copolymers including polyethylene oxides (PEO); polyesters including polyethylene terephthalates, polybutylene terephthalates and aliphatic polyesters such as polymers and copolymers of lactide (which includes lactic acid as well as d-,l- and meso lactide), epsilon-caprolactone, glycolide (including glycolic acid), hydroxybutyrate, hydroxyvalerate, para-dioxanone, trimethylene carbonate (and its alkyl derivatives), 1,4-dioxepan-2-one, 1,5-dioxepan-2-one, and 6,6-dimethyl-1,4-dioxan-2-one (a copolymer of polylactic acid and polycaprolactone is one specific example); polyether polymers and copolymers including polyarylethers such as polyphenylene ethers, polyether ketones, polyether ether ketones; polyphenylene sulfides; polyisocyanates; polyolefin polymers and copolymers, including polyalkylenes such as polypropylenes, polyethylenes (low and high density, low and high molecular weight), polybutylenes (such as polybut-1-ene and polyisobutylene), polyolefin elastomers (e.g., santoprene), ethylene propylene diene monomer (EPDM) rubbers, poly-4-methyl-pen-1-enes, ethylene-alpha-olefin copolymers, ethylene-methyl methacrylate copolymers and ethylene-vinyl acetate copolymers; fluorinated polymers and copolymers, including polytetrafluoroethylenes (PTFE), poly(tetrafluoroethylene-co-hexafluoropropene) (FEP), modified ethylene-tetrafluoroethylene copolymers (ETFE), and polyvinylidene fluorides (PVDF); silicone polymers and copolymers; polyurethanes; p-xylylene polymers; polyiminocarbonates; copoly(ether-esters) such as polyethylene oxide-polylactic acid copolymers; polyphosphazines; polyalkylene oxalates; polyoxaamides and polyoxaesters (including those containing amines and/or amino groups); polyorthoesters; biopolymers, such as polypeptides, proteins, polysaccharides and fatty acids (and esters thereof), including fibrin, fibrinogen, collagen, elastin, chitosan, gelatin, starch, glycosaminoglycans such as hyaluronic acid; as well as blends and further copolymers of the above.

As previously noted, a variety of different techniques may be employed to form the depressions or to sculpt a medical device from the substrate (e.g., to sculpt stent struts from tubes). For example, such techniques include direct removal techniques as well as mask-based removal techniques, in which masking is used to protect material that is not to be removed. Direct removal techniques include those in which material is removed through contact with solid tools (e.g., microdrilling, micromachining, etc., using high precision equipment such as high precision milling machines and lathes) and those that remove material without the need for solid tools (e.g., those based on directed energetic beams such as laser, electron, and ion beams). In the latter cases, techniques based on diffractive optical elements (DOEs), holographic diffraction, and/or polarization trepanning, among other beam manipulation methods, may be employed to generate patterns as desired. Using these and other techniques, multiple depressions can be formed in a material layer at once.

Mask-based techniques include those in which the masking material contacts the material to be machined (e.g., where masks are formed using known lithographic techniques, including optical, ultraviolet, deep ultraviolet, electron beam, and x-ray lithography) and techniques in which the masking material does not contact the material to be machined, but which is provided between a directed source of excavating energy and the material to be machined (e.g., opaque masks having apertures formed therein, as well as semi-transparent masks such as gray-scale masks which provide variable beam intensity and thus variable machining rates). One process, known as collimated plasma lithography, is capable of producing X-rays for lithography having wavelengths on the order of 10 nm. Material is removed in regions not protected by the above masks using any of a range of processes including physical processes (e.g., thermal sublimation and/or vaporization of the material that is removed), chemical processes (e.g., chemical breakdown and/or reaction of the material that is removed), or a combination of both. Specific examples of removal processes include wet and dry (plasma) etching techniques, and ablation techniques based on directed energetic beams such as electron, ion and laser beams. A lithography-based process for forming nanoporous silicon is described, for example, in L. Leoni et al. "Nanoporous Platforms for Cellular Sensing and Delivery," Sensors 2002, 2, 111-120.

In those embodiments of the invention where laser light is used for material removal (e.g., for formation of depressions, stent struts, etc.), shorter wavelength light may be preferred. There are several reasons for this. For example, shorter wavelength light such as UV and deep-UV light can be imaged to a smaller spot size than light of longer wavelengths (e.g., because the minimum feature size is limited by diffraction, which increases with wavelength). Such shorter wavelength light is also typically relatively photolytic, displaying less thermal influence on surrounding material. Moreover, many materials have high absorption coefficients in the ultraviolet region. This means that the penetration depth is small, with each pulse removing only a thin layer of material, thereby allowing precise control of the drilling depth. Various lasers are available for laser ablation, including excimer lasers, solid state lasers such as those based on Nd:YAG and Nd:vanadate, among other crystals, metal vapor lasers, such as copper vapor lasers, and femtosecond lasers. Further information on lasers and laser ablation may be found in T. Lippert et al., "Chemical and spectroscopic aspects of polymer ablation: Special features and novel directions," Chem. Rev., 103(2): 453-485 February 2003; J. Meijer et al., "Laser Machining by short and ultrashort pulses, state of the art and new opportunities in the age of photons," Annals of the CIRP, 51(2), 531-550, 2002, and U.S. Pat. No. 6,517,888 to Weber.

It is noted that there is a great amount of available know-how in the semiconductor industry for etching holes (e.g., vias), trenches and other voids in various materials. For this reason, in some embodiments of the invention, material may be removed from materials for which processing is routine in the semiconducting industry including semiconducting materials such as silicon, conductive materials such as metals and metal alloys, and insulating materials such as silicon oxide, silicon nitride and various metal oxides.

"Biologically active agents," "drugs," "therapeutic agents," "pharmaceutically active agents," "pharmaceutically active materials," and other related terms may be used interchangeably herein and include genetic therapeutic agents, non-genetic therapeutic agents and cells. A wide variety of therapeutic agents can be employed in conjunction with the present invention. Numerous therapeutic agents are described here.

Suitable non-genetic therapeutic agents for use in connection with the present invention may be selected, for example, from one or more of the following: (a) anti-thrombotic agents such as heparin, heparin derivatives, urokinase, clopidogrel, and PPack (dextrophenylalanine proline arginine chloromethylketone); (b) anti-inflammatory agents such as dexamethasone, prednisolone, corticosterone, budesonide, estrogen, sulfasalazine and mesalamine; (c) antineoplastic/antiproliferative/anti-miotic agents such as paclitaxel, 5-fluorouracil, cisplatin, vinblastine, vincristine, epothilones, endostatin, angiostatin, angiopeptin, monoclonal antibodies capable of blocking smooth muscle cell proliferation, and thymidine kinase inhibitors; (d) anesthetic agents such as lidocaine, bupivacaine and ropivacaine; (e) anti-coagulants such as D-Phe-Pro-Arg chloromethyl ketone, an RGD peptide-containing compound, heparin, hirudin, antithrombin compounds, platelet receptor antagonists, anti-thrombin antibodies, anti-platelet receptor antibodies, aspirin, prostaglandin inhibitors, platelet inhibitors and tick antiplatelet peptides; (f) vascular cell growth promoters such as growth factors, transcriptional activators, and translational promotors; (g) vascular cell growth inhibitors such as growth factor inhibitors, growth factor receptor antagonists, transcriptional repressors, translational repressors, replication inhibitors, inhibitory antibodies, antibodies directed against growth factors, bifunctional molecules consisting of a growth factor and a cytotoxin, bifunctional molecules consisting of an antibody and a cytotoxin; (h) protein kinase and tyrosine kinase inhibitors (e.g., tyrphostins, genistein, quinoxalines); (i) prostacyclin analogs; (j) cholesterol-lowering agents; (k) angiopoietins; (l) antimicrobial agents such as triclosan, cephalosporins, aminoglycosides and nitrofurantoin; (m) cytotoxic agents, cytostatic agents and cell proliferation affectors; (n) vasodilating agents; (o) agents that interfere with endogenous vasoactive mechanisms; (p) inhibitors of leukocyte recruitment, such as monoclonal antibodies; (q) cytokines; (r) hormones; (s) inhibitors of HSP 90 protein (i.e., Heat Shock Protein, which is a molecular chaperone or housekeeping protein and is needed for the stability and function of other client proteins/signal transduction proteins responsible for growth and survival of cells) including geldanamycin, (t) smooth muscle relaxants such as alpha receptor antagonists (e.g., doxazosin, tamsulosin, terazosin, prazosin and alfuzosin), calcium channel blockers (e.g., verapimil, diltiazem, nifedipine, nicardipine, nimodipine and bepridil), beta receptor agonists (e.g., dobutamine and salmeterol), beta receptor antagonists (e.g., atenolol, metaprolol and butoxamine), angiotensin-II receptor antagonists (e.g., losartan, valsartan, irbesartan, candesartan, eprosartan and telmisartan), and antispasmodic/anticholinergic drugs (e.g., oxybutynin chloride, flavoxate, tolterodine, hyoscyamine sulfate, diclomine), (u) bARKct inhibitors, (v) phospholamban inhibitors, (w) Serca 2 gene/protein, (x) immune response modifiers including aminoquizolines, for instance, imidazoquinolines such as resiquimod and imiquimod, (y) human apolioproteins (e.g., AI, AII, AIII, AIV, AV, etc.), (z) selective estrogen receptor modulators (SERMs) such as raloxifene, lasofoxifene, arzoxifene, miproxifene, ospemifene, PKS 3741, MF 101 and SR 16234, (aa) PPAR agonists such as rosiglitazone, pioglitazone, netoglitazone, fenofibrate, bexaotene, metaglidasen, rivoglitazone and tesaglitazar, (bb) prostaglandin E agonists such as alprostadil or ONO 8815Ly, (cc) thrombin receptor activating peptide (TRAP), (dd) vasopeptidase inhibitors including benazepril, fosinopril, lisinopril, quinapril, ramipril, imidapril, delapril, moexipril and spirapril, (ee) thymosin beta 4, and (ff) phospholipids including phosphorylcholine, phosphatidylinositol and phosphatidylcholine.

Preferred non-genetic therapeutic agents include taxanes such as paclitaxel (including particulate forms thereof, for instance, protein-bound paclitaxel particles such as albumin-bound paclitaxel nanoparticles, e.g., ABRAXANE), sirolimus, everolimus, tacrolimus, zotarolimus, Epo D, dexamethasone, estradiol, halofuginone, cilostazole, geldanamycin, ABT-578 (Abbott Laboratories), trapidil, liprostin, Actinomcin D, Resten-NG, Ap-17, abciximab, clopidogrel, Ridogrel, beta-blockers, bARKct inhibitors, phospholamban inhibitors, Serca 2 gene/protein, imiquimod, human apolioproteins (e.g., AI-AV), growth factors (e.g., VEGF-2), as well derivatives of the forgoing, among others.

Suitable genetic therapeutic agents for use in connection with the present invention include anti-sense DNA and RNA as well as DNA coding for the various proteins (as well as the proteins themselves) and may be selected, for example, from one or more of the following: (a) anti-sense RNA, (b) tRNA or rRNA to replace defective or deficient endogenous molecules, (c) angiogenic and other factors including growth factors such as acidic and basic fibroblast growth factors, vascular endothelial growth factor, endothelial mitogenic growth factors, epidermal growth factor, transforming growth factor α and β, platelet-derived endothelial growth factor, platelet-derived growth factor, tumor necrosis factor α, hepatocyte growth factor and insulin-like growth factor, (d) cell cycle inhibitors including CD inhibitors, and (e) thymidine kinase ("TK") and other agents useful for interfering with cell proliferation. Also of interest is DNA encoding for the family of bone morphogenic proteins ("BMP's"), including BMP-2, BMP-3, BMP-4, BMP-5, BMP-6 (Vgr-1), BMP-7 (OP-1), BMP-8, BMP-9, BMP-10, BMP-11, BMP-12, BMP-13, BMP-14, BMP-15, and BMP-16. Currently preferred BMP's are any of BMP-2, BMP-3, BMP-4, BMP-5, BMP-6 and BMP-7. These dimeric proteins can be provided as homodimers, heterodimers, or combinations thereof, alone or together with other molecules. Alternatively, or in addition, molecules capable of inducing an upstream or downstream effect of a BMP can be provided. Such molecules include any of the "hedgehog" proteins, or the DNA's encoding them.

Vectors for delivery of genetic therapeutic agents include viral vectors such as adenoviruses, gutted adenoviruses, adeno-associated virus, retroviruses, alpha virus (Semliki Forest, Sindbis, etc.), lentiviruses, herpes simplex virus, replication competent viruses (e.g., ONYX-015) and hybrid vectors; and non-viral vectors such as artificial chromosomes and mini-chromosomes, plasmid DNA vectors (e.g., pCOR), cationic polymers (e.g., polyethyleneimine, polyethyleneimine (PEI)), graft copolymers (e.g., polyether-PEI and polyethylene oxide-PEI), neutral polymers such as polyvinylpyrrolidone (PVP), SPI017 (SUPRATEK), lipids such as cationic lipids, liposomes, lipoplexes, nanoparticles, or microparticles, with and without targeting sequences such as the protein transduction domain (PTD).

Cells for use in conjunction with the present invention include cells of human origin (autologous or allogeneic), including whole bone marrow, bone marrow derived mononuclear cells, progenitor cells (e.g., endothelial progenitor cells), stem cells (e.g., mesenchymal, hematopoietic, neuronal), pluripotent stem cells, fibroblasts, myoblasts, satellite cells, pericytes, cardiomyocytes, skeletal myocytes or macrophage, or from an animal, bacterial or fungal source (xenogeneic), which can be genetically engineered, if desired, to deliver proteins of interest.

Further therapeutic agents, not necessarily exclusive of those listed above, have been identified as candidates for vascular treatment regimens, for example, as agents targeting restenosis (anti-restenotic agents). Suitable agents may be selected, for example, from one or more of the following: (a) Ca-channel blockers including benzothiazapines such as diltiazem and clentiazem, dihydropyridines such as nifedipine, amlodipine and nicardapine, and phenylalkylamines such as verapamil, (b) serotonin pathway modulators including: 5-HT antagonists such as ketanserin and naftidrofuryl, as well as 5-HT uptake inhibitors such as fluoxetine, (c) cyclic nucleotide pathway agents including phosphodiesterase inhibitors such as cilostazole and dipyridamole, adenylate/Guanylate cyclase stimulants such as forskolin, as well as adenosine analogs, (d) catecholamine modulators including α-antagonists such as prazosin and bunazosine, β-antagonists such as propranolol and α/β-antagonists such as labetalol and carvedilol, (e) endothelin receptor antagonists such as bosentan, sitaxsentan sodium, atrasentan, endonentan, (f) nitric oxide donors/releasing molecules including organic nitrates/nitrites such as nitroglycerin, isosorbide dinitrate and amyl nitrite, inorganic nitroso compounds such as sodium nitroprusside, sydnonimines such as molsidomine and linsidomine, nonoates such as diazenium diolates and NO adducts of alkanediamines, S-nitroso compounds including low molecular weight compounds (e.g., S-nitroso derivatives of captopril, glutathione and N-acetyl penicillamine) and high molecular weight compounds (e.g., S-nitroso derivatives of proteins, peptides, oligosaccharides, polysaccharides, synthetic polymers/oligomers and natural polymers/oligomers), as well as C-nitroso-compounds, O-nitroso-compounds, N-nitroso-compounds and L-arginine, (g) Angiotensin Converting Enzyme (ACE) inhibitors such as cilazapril, fosinopril and enalapril, (h) ATH-receptor antagonists such as saralasin and losartin, (i) platelet adhesion inhibitors such as albumin and polyethylene oxide, (j) platelet aggregation inhibitors including cilostazole, aspirin and thienopyridine (ticlopidine, clopidogrel) and GP IIb/IIIa inhibitors such as abciximab, epitifibatide and tirofiban, (k) coagulation pathway modulators including heparinoids such as heparin, low molecular weight heparin, dextran sulfate and β-cyclodextrin tetradecasulfate, thrombin inhibitors such as hirudin, hirulog, PPACK(D-phe-L-propyl-L-arg-chloromethylketone) and argatroban, FXa inhibitors such as antistatin and TAP (tick anticoagulant peptide), Vitamin K inhibitors such as warfarin, as well as activated protein C, (l) cyclooxygenase pathway inhibitors such as aspirin, ibuprofen, flurbiprofen, indomethacin and sulfinpyrazone, (m) natural and synthetic corticosteroids such as dexamethasone, prednisolone, methprednisolone and hydrocortisone, (n) lipoxygenase pathway inhibitors such as nordihydroguairetic acid and caffeic acid, (o) leukotriene receptor antagonists, (p) antagonists of E- and P-selectins, (q) inhibitors of VCAM-1 and ICAM-1 interactions, (r) prostaglandins and analogs thereof including prostaglandins such as PGE1 and PGI2 and prostacyclin analogs such as ciprostene, epoprostenol, carbacyclin, iloprost and beraprost, (s) macrophage activation preventers including bisphosphonates, (t) HMG-CoA reductase inhibitors such as lovastatin, pravastatin, atorvastatin, fluvastatin, simvastatin and cerivastatin, (u) fish oils and omega-3-fatty acids, (v) free-radical scavengers/antioxidants such as probucol, vitamins C and E, ebselen, trans-retinoic acid and SOD (orgotein), SOD mimics, verteporfin, rostaporfin, AGI 1067, and M 40419, (w) agents affecting various growth factors including FGF pathway agents such as bFGF antibodies and chimeric fusion proteins, PDGF receptor antagonists such as trapidil, IGF pathway agents including somatostatin analogs such as angiopeptin and ocreotide, TGF-β pathway agents such as polyanionic agents (heparin, fucoidin), decorin, and TGF-β antibodies, EGF pathway agents such as EGF antibodies, receptor antagonists and chimeric fusion proteins, TNF-α pathway agents such as thalidomide and analogs thereof, Thromboxane A2 (TXA2) pathway modulators such as sulotroban, vapiprost, dazoxiben and ridogrel, as well as protein tyrosine kinase inhibitors such as tyrphostin, genistein and quinoxaline derivatives, (x) matrix metalloprotease (MMP) pathway inhibitors such as marimastat, ilomastat, metastat, batimastat, pentosan polysulfate, rebimastat, incyclinide, apratastat, PG 116800, RO 1130830 or ABT 518, (y) cell motility inhibitors such as cytochalasin B, (z) antiproliferative/antineoplastic agents including antimetabolites such as purine analogs (e.g., 6-mercaptopurine or cladribine, which is a chlorinated purine nucleoside analog), pyrimidine analogs (e.g., cytarabine and 5-fluorouracil) and methotrexate, nitrogen mustards, alkyl sulfonates, ethylenimines, antibiotics (e.g., daunorubicin, doxorubicin), nitrosoureas, cisplatin, agents affecting microtubule dynamics (e.g., vinblastine, vincristine, colchicine, Epo D, paclitaxel and epothilone), caspase activators, proteasome inhibitors, angiogenesis inhibitors (e.g., endostatin, angiostatin and squalamine), rapamycin (sirolimus) and its analogs (e.g., everolimus, tacrolimus, zotarolimus, etc.), cerivastatin, flavopiridol and suramin, (aa) matrix deposition/organization pathway inhibitors such as halofuginone or other quinazolinone derivatives, pirfenidone and tranilast, (bb) endothelialization facilitators such as VEGF and RGD peptide, (cc) blood rheology modulators such as pentoxifylline and (dd) glucose cross-link breakers such as alagebrium chloride (ALT-711).

Numerous additional therapeutic for the practice of the present invention may be selected from suitable therapeutic agents disclosed in U.S. Pat. No. 5,733,925 to Kunz.

Although various embodiments are specifically illustrated and described herein, it will be appreciated that modifications and variations of the present invention are covered by the above teachings and are within the purview of the appended claims without departing from the spirit and intended scope of the invention.

The invention claimed is:

1. An implantable or insertable medical device comprising as components: (a) a substrate component comprising a depression, and (b) a pre-formed filter insert that is at least partially filled with a therapeutic agent-containing material that comprises a first therapeutic agent and disposed in the depression such that it regulates transport of chemical species between the depression and an exterior of the device upon implantation or insertion of the device in vivo, wherein the pre-formed filter insert comprises a hollow reservoir extending through a portion of the pre-formed filter insert to a porous base and is configured to be preloaded with the therapeutic agent-containing material before being disposed in the depression.

2. The implantable or insertable medical device of claim 1 further comprising a welded braze securing the filter insert in the depression.

3. The implantable or insertable medical device of claim 1 wherein the pre-formed filter insert is configured so that it is secured in the depression by an interference fit.

4. The implantable or insertable medical device of claim 1 wherein an opening into the depression has a peripheral lip that engages with the filter insert to secure the filter insert within the depression.

5. The implantable or insertable medical device of claim 1 wherein the filter insert includes an assembly having a porous base and at least one channel extending through the assembly to the porous base through which the porous base is loaded with the therapeutic agent-containing material.

6. The implantable or insertable medical device of claim 1, wherein said substrate component comprises a plurality of depressions.

7. The implantable or insertable medical device of claim 1, wherein said depression is a blind hole or a trench.

8. The implantable or insertable medical device of claim 1, wherein said medical device is adapted for implantation or insertion into a coronary vasculature, peripheral vascular system, esophagus, trachea, colon, biliary tract, urogenital system, or brain.

9. The implantable or insertable medical device of claim 1, wherein said medical device is selected from a drug delivery device, an implant, a stent, a graft, a filter, a catheter, a defibrillator, a chronic rhythm management lead and a neuromodulation device.

10. The implantable or insertable medical device of claim 1, wherein the therapeutic agent-containing material further comprises a material in addition to said first therapeutic agent.

11. The implantable or insertable medical device of claim 10, wherein the therapeutic agent-containing material further comprises a second therapeutic agent.

12. The implantable or insertable medical device of claim 1, wherein said therapeutic agent is selected from one or more of the group consisting of anti-thrombotic agents, anti-proliferative agents, anti-inflammatory agents, anti-restenotic agents, anti-migratory agents, agents affecting extracellular matrix production and organization, antineoplastic agents, anti-mitotic agents, anesthetic agents, anti-coagulants, vascular cell growth promoters, vascular cell growth inhibitors, cholesterol-lowering agents, vasodilating agents, TGF-$\beta$ elevating agents, and agents that interfere with endogenous vasoactive mechanisms.

13. The implantable or insertable medical device of claim 1 wherein the pre-formed filter insert includes a nanoporous region.

14. The implantable or insertable medical device of claim 1 wherein a smallest lateral dimension of the depression is less than 10,000 microns.

15. A method of making the implantable or insertable medical device of claim 1, comprising (a) at least partially filling the depression with the therapeutic agent-containing material, and (b) inserting the pre-formed filter insert into the depression over the therapeutic agent-containing material.

16. A method of making the implantable or insertable medical device of claim 1, comprising (a) impregnating the pre-formed filter insert with the therapeutic agent-containing material, and (b) inserting the impregnated pre-formed filter insert into the depression.

17. The implantable or insertable medical device of claim 16 further comprising securing the pre-formed filter insert within the depression.

18. The implantable or insertable medical device of claim 16 wherein the pre-formed filter insert is secured within the depression using a welding technique.

19. The implantable or insertable medical device of claim 16 wherein the pre-formed filter insert includes a reservoir housing and further comprising loading the reservoir housing with the therapeutic agent-containing material and plugging the reservoir housing with a filter material.

20. The implantable or insertable medical device of claim 19 wherein the reservoir housing is plugged with the filter material prior to inserting the impregnated pre-formed filter insert into the depression.

21. An implantable or insertable medical device comprising as components: (a) a substrate component comprising a depression that is at least partially filled with a therapeutic agent-containing material that comprises a first therapeutic agent, and (b) a pre-formed filter insert that is at least partially filled with a therapeutic agent-containing material that comprises a first therapeutic agent and disposed in the depression such that it regulates transport of chemical species between the depression and an exterior of the device upon implantation or insertion of the device in vivo, wherein the pre-formed filter insert comprises a hollow reservoir extending through a portion of the pre-formed filter insert to a porous base and is configured to be preloaded with the therapeutic agent-containing material before being disposed in the depression and the pre-formed filter insert is configured so that it is secured in the depression by an interference fit.

22. An implantable or insertable medical device comprising as components: (a) a substrate component comprising a depression that is at least partially filled with a therapeutic agent-containing material that comprises a first therapeutic agent, and (b) a pre-formed filter insert disposed in the depression such that it regulates transport of chemical species between the depression and an exterior of the device upon implantation or insertion of the device in vivo, wherein the pre-formed filter insert is disposed in the depression over the therapeutic agent-containing material, said pre-formed filter insert including an assembly having a porous base and at least one channel extending through the assembly to the porous base through which the porous base is loaded with the therapeutic agent-containing material.

23. An implantable or insertable medical device comprising as components: (a) a substrate component comprising a depression, and (b) a pre-formed filter insert disposed in the depression such that the pre-formed filter insert regulates transport of chemical species between the depression and an exterior of the device upon implantation or insertion of the device in vivo, wherein the filter insert includes an assembly having a porous base and a plurality of channels extending through the assembly to the porous base through which the porous base is loaded with a therapeutic agent-containing material.

* * * * *